United States Patent [19]

Perrier et al.

[11] Patent Number: 5,562,924

[45] Date of Patent: Oct. 8, 1996

[54] POLYSACCHARIDE WALL MICROCAPSULES CONTAINING PRIMARY ALCOHOL FUNCTIONS AND COMPOSITIONS CONTAINING SAME

[75] Inventors: Eric Perrier, Vienne; Chantal Buffevant, Millery, both of France

[73] Assignee: Coletica, France

[21] Appl. No.: 295,886

[22] PCT Filed: Mar. 10, 1993

[86] PCT No.: PCT/FR93/00237

§ 371 Date: Sep. 8, 1994

§ 102(e) Date: Sep. 8, 1994

[87] PCT Pub. No.: WO93/17784

PCT Pub. Date: Sep. 16, 1993

[30] Foreign Application Priority Data

Mar. 11, 1992 [FR] France ................................. 92 02912

[51] Int. Cl.⁶ ........................... B01J 13/08; A61K 9/50
[52] U.S. Cl. ..................... 424/499; 264/4.1; 264/4.3; 427/213.3
[58] Field of Search ............... 264/4.1, 4.3; 424/499; 427/213.3

[56] References Cited

PUBLICATIONS

Levy et al., J. Microencapsalation (1991), 8 (3), 335–47.

*Primary Examiner*—Nathan M. Nutter
*Attorney, Agent, or Firm*—Dvorak and Traub

[57] ABSTRACT

The invention concerns the production of polysaccharide wall microcapsules or microspheres containing primary alcohol functions crosslinked by a crosslinking agent. Said microcapsules or microspheres contain an active food, cosmetic or pharmaceutical ingredient and are hence used in the preparation of food, cosmetic or pharmaceutical compositions.

25 Claims, No Drawings

POLYSACCHARIDE WALL MICROCAPSULES CONTAINING PRIMARY ALCOHOL FUNCTIONS AND COMPOSITIONS CONTAINING SAME

The present invention relates essentially to the use of polysaccharides having primary alcohol functions for the production of microcapsules or microspheres, to the microcapsules and microspheres thus produced, to a method for producing such microcapsules or microspheres and to cosmetic, pharmaceutic or food compositions containing them.

The Applicant has already described in document FR-A-2 642 329 the use of solutions of atelocollagen and of glycosaminoglycans for producing microcapsules, the microcapsules themselves, their production method as well as cosmetic, pharmaceutical or food compositions containing same.

Such microcapsules with mixed wall of atelocollagen and glycosaminoglycan are totally satisfactory.

However, it may be advantageous in certain cases, to use microcapsules or microspheres produced from materials issued from plants or obtained by microbial fermentation.

It has also been proposed to produce microcapsules by interfacial polymerization of synthetic monomer, more particularly on synthetic diamines so as to form amide functions in the same way as during the chemical synthesis of Nylon, thus permitting a strong enevelope to be constituted around the capsule. The core of the capsule is not involved in the polymerization reaction and can be constituted of protein (FR-76 34 482 and FR-79 2012) of polysaccharide (U.S. Pat No. 4,322,311).

It has also been proposed to produce capsules from proteins crosslinked by diacid derivatives (FR-A-1 415 039) or by glutaraldehyde (WO-82/00660).

It has also been proposed to produce capsules of which the wall contains polysaccharides ionically crosslinked by mono-, di- or trivalent cations (U.S. Pat. No. 4,495,288) or with polycationic molecules of high molecular weight (EP-A1-0 301 777; U.S. Pat. No. 4,407,957; U.S. Pat. No. 4,391,309).

It has also been proposed to produce capsules based on amino polysaccharides, for example chitosan, crosslinked with bifunctional agents such as glutaraldehyde (WO-82/00660).

It is the object of the present invention to solve the new technical problem consisting in providing a solution for producing microcapsules or microspheres containing a basic material of excellent biocompatibility, total biodegradability, total assimilation, total innocuousness, which comes from a renewable biological material, and can be found not only in animals but also in plants and which can also be produced by microbial fermentation.

This new technical problem has been solved for the first time in a satisfactory and inexpensive manner, usable at the industrial level, notably at the food, cosmetic or pharmaceutical level.

Thus, in a first aspect, the present invention relates to the use of polysaccharides having primary alcohol functions, for producing microcapsules or microspheres which preferably contain an active ingredient which may be for example a food, cosmetic or pharmaceutical one. In this respect, the polysaccharides with primary alcohol functions preferably have a molecular weight higher than 5,000 Daltons. Moreover, said polysaccharides with primary alcohol functions advantageously have between 1 and 4 primary alcohol functions per diosidic moiety.

In a second aspect, the present invention also relates to microcapsules or microspheres characterized in that they comprise a wall in polysaccharide having primary alcohol functions which are crosslinked preferably by interfacial crosslinking, using a crosslinking agent preferably constituted by an acid dichloride or an acid anhydride.

According to an advantageous embodiment, said polysaccharide with primary alcohol function has a molecular weight greater than 5,000 Daltons.

According to a preferred embodiment, said polysaccharide comprises between 1 and 4 primary alcohol functions per diosodic moiety.

According to a particular embodiment, said polysaccharides with primary alcohol function are selected from the group consisting in:

(a) the natural polysaccharides or the polysaccharides obtained by fermentation, in particular:

the galactomannans, for example the galactomannans issued from guar such as Viscogum® (SANOFI), or from carob such as those commercially available under the name Lygomme® (SANOFI) or Meypro-Fleur®, or Meyprodyn® (MEYHALL);

the carrageenans such as those extracted from red algaes like those commercially available under the name Satiagel® or Satiagum® (SANOFI);

the glucomannans, such as those issued from KONJAC, like those commercially available under the name Nutricol® (FMC Corporation) or Propol® (SHIMITZU);

the natural gums;

the amylose or amylopectine and their mixtures which are extracted from plants or from their fruits such as for example corn, maize, pea or potato;

the polysaccharides with primary alcohol function issued from fermentation such as Xanthane (KELKO), Gellane® (KELKO) or Curdlane®(TAKEDA).

(b) The polysaccharides modified chemically by fixation or by creation of primary alcohol on the polymer.

It may indeed be very advantageous to introduce primary alcohol groups acting as spacing arm spacing out primary alcohol groups from the polymer skeleton in order to make them more accessible, notably for a possible reaction with the crosslinking agent, as will be described hereinafter with reference to the production method.

A suitable example of primary alcohol group is a $C_1$–$C_{30}$ and in particular a $C_1$–$C_6$ hydroxyalkyl radical.

Examples of chemically modified polysaccharides are celluloses at least partly etherified by alkylhydroxy radicals, in particular by etherification with one or more hydroxy functions of the cellulosic molecule with a corresponding alkylene oxide as understable to the man skilled in the art. Particularly advantageous and easy-to-use etherification agents are, the methylene, ethylene, propylene, butylene oxides. Moreover, chemically modified polysaccharides of this type are commercially available, such as for example the Natrosol type hydroxyethylcelluloses, sold by the company Aqualon. It is thus understood that the invention is not in any way limited to a special list of chemically modified polysaccharides but that it covers all the polysaccharides that are chemically modified in order to make the primary alcohol functions more readily available.

According to an advantageous embodiment, said microcapsules or microspheres contain a water-soluble, water-dispersible, non-soluble or liposoluble active ingredient, which is either present in the wall of the microcapsules or microspheres, or else which is encapsulated within said microcapsules or microspheres. It may be a food, cosmetic or pharmaceutical active ingredient.

In a third aspect, the present invention also provides a method for producing said microcapsules or microspheres, characterized in that it comprises dispersing or dissolving a polysaccharide having primary alcohol functions in aqueous phase, then obtaining an aqueous phase which contains said polysaccharide in dispersion or in dissolved state, then placing said aqueous phase containing the polysaccharide in contact with an organic phase non-miscible in water and containing a crosslinking agent having functions capable of reacting preferentially with the primary alcohol functions of the polysaccharide, in order to produce an interfacial crosslinking between the primary alcohol functions of the polysaccharide and the reactive functions of the crosslinking agent, for a long enough period to obtain said microspheres or microcapsules, which are thereafter separated from the reaction medium by any separation means.

According to a variant embodiment of the method according to the invention, the crosslinking agent is an acid dichloride or an acid dianhydride, thus forming ester bonds. According to a preferred characteristic, the crosslinking agent is selected from terephtalic acid dichloride, phtalic acid dichloride, sebacic acid dichloride, succinic acid dichloride, tricarboxylic acid dichloride or trichloride such as citric acid or an acid dianhydride such as succinic dianhydride.

According to another particular embodiment of the method according to the invention, the organic phase which is non-soluble in water or hydrophobic comprises a vegetable oil, a fatty acid ester, a mineral oil, a silicone or an apolar organic solvent, in particular hexane, cyclohexane or chloroform.

According to another particularly advantageous embodiment of the invention, the polysaccharide used according to the invention containing primary alcohol functions has a molecular weight higher than 5,000 Daltons.

According to another particular variant of embodiment, the concentration of polysaccharide with primary alcohol function ranges between 0.2% and 30% by weight of the aqueous phase.

According to another particularly advantageous variant of the method according to the invention, the aqueous phase is an alkaline aqueous phase, namely a phase whose pH is an alkaline pH, hence a pH higher than 7. A preferred pH range is one where the pH is between about 7.1 and about 10.

A suitable base to use in order to bring the aqueous phase to a basic pH is an ammonia, borate, phosphate or carbonate buffer.

According to a particularly advantageous variant of embodiment, said preferably basic aqueous phase is emulsified, optionally with an emulsifying agent in an oily phase. As emulsifying agent, it is possible to use for example the products sold by ICI such as "SPAN®", "TWEEN®", "BRIJ®", "ARLACEL®".

The proportions by weight of crosslinking agent to be used with respect to the weight of the polysaccharide solution used vary between 20 and 60 but they are preferably situated between 30 and 45%.

The interfacial crosslinking time can vary within wide limits and is dependent on the basic material used, on the crosslinking agent, on the nature of the phases as well as on the dimensions wanted for the microcapsules or microspheres. Said interfacial crosslinking time is relatively long and will generally vary between 15 minutes and 24 hours and is in particular close to 90 minutes.

According to another advantageous variant of embodiment, it is possible to mix intimately with the aqueous phase containing the polysaccharide, a water-soluble, water-dispersible, non-soluble or liposoluble active ingredient. In particular, said active ingredient can be a food, cosmetic or pharmaceutical active ingredient.

In the case of a liposoluble active ingredient, it is also possible to use a an emulsion-stabilizing agent such as a colloid, a macromolecule, a synthetic or natural emulsifying agent.

According to a particular variant of embodiment, when the polysaccharide is not soluble at room temperature in the aqueous preferably alkaline phase, it is possible to proceed to a heating step for a long enough period to dissolve the whole of the polysaccharide, and then to cool the aqueous phase down to room temperature. In general, a heating to about 90° C. for one hour is sufficient to dissolve all the polysaccharide.

Separation of the spheres or capsules obtained after crosslinking can be achieved by any appropriate means, and in particular by natural decantation of by centrifuging.

It is also possible to carry out one or more washes of said spheres or capsules.

According to a particular variant of embodiment, the spheres or capsules can also be placed in suspension in a gel, a silicon phase or a liquid phase, depending on the proposed applications.

The spheres or capsules based on crosslinked polysaccharide with primary alcohol function according to the invention can also be used in food, cosmetic or pharmaceutical formulations.

Thus in a fourth aspect, the present invention also covers a food, cosmetic or pharmaceutical composition, characterized in that it comprises microcapsules or microspheres with wall in polysaccharide having primary alcohol functions which are crosslinked by a crosslinking agent and which preferably contain at least partly a substance presenting a food, cosmetic or pharmaceutical advantage.

In a fifth aspect, the present invention also covers a method for preparing a food, pharmaceutical or cosmetic composition, characterized in that it comprises using at least partly microcapsules with a wall in polysaccharide having primary alcohol functions crosslinked by a crosslinking agent, containing preferably at least partly a substance presenting a food, cosmetic or pharmaceutical advantage, optionally in a excipient acceptable for use with food, cosmetics or pharmaceutics.

The size of the capsules or spheres will generally be between 5 μm and 900 μm. The size of the capsules or spheres can be adjusted by adjusting the stirring speed during the interfacial crosslinking, as is wellknown to the man skilled in the art.

In the description and the claims, the word microcapsules or microspheres are used indifferently in an equivalent manner to designate particles comprising on the inside a space permitting the encapsulation of an active ingredient, particularly in an aqueous or non-aqueous phase.

The capsules or spheres according to the present invention, based on polysaccharide containing primary alcohol functions, present an excellent biocompatibility since the polysaccharides used are not cytotoxic, a total biodegradability since the polysaccharides used are readily biodegradable, for example by bacterial amylases; their assimilation is total since the degradation residues are simple oses which can be used directly by the cell as source of energy; their toxicity is virtually nil since the oral, skin, eye irritation tests which were conducted by the inventors have shown their total innocuousness in vitro and in vivo in animals.

Moreover, the polysaccharides with primary alcohol functions are obtained from renewable biological materials.

They are widespread in the nature where they are found not only in animals, but also in micro-organisms as well as in higher plants and in algae where they represent more than 75% of their dry weight.

Also, the polysaccharides make it very easy to trap the active ingredients, including those of low molecular weight, either in the wall, or by encapsulation inside the spheres or capsules.

The invention makes it possible to use polysaccharides with primary alcohol function originating in particular from microbial fermentation or from plants, thus eliminating the need to use products extracted from animals.

The invention also makes it possible to use chemically modified polysaccharides which contain primary alcohol functions that are more readily accessible owing to the introduction of spacer arms as described hereinabove. Said primary alcohol groups can be added to already existing alcohol functions, by etherification, or they can be created on the polymer structure.

In the case of the present invention, pharmaceutical use designates the pharmaceutical use in animal medicine as well as in human medicine.

Other objects, characteristics and advantages of the invention will emerge clearly from the following explanatory description given with reference to several examples of the invention given solely by way of illustration and which could not possibly limit in any way the scope of the invention. In the examples, the percentages are given by weight except otherwise stated.

EXAMPLE 1

Standard polysaccharide-based spheres (5 to 900 μm)

1. A preparation of carob polysaccharide is prepared as follows:

6.4 kg of carob flour (Lygomme, SANOFI) are placed in suspension in 400 kg of cold deionized water. The preparation is heated to 90° C. for one hour in order to obtain a complete solvation of the polysaccharide-containing chains. The very viscous solution which is obtained is left to cool down to room temperature. 20 kg of $NaHCO_3$ are then added to the preparation under strong stirring. After complete dissolution, the pH is stabilized to a value ranging between 8 and 8.4.

2. Preparation of the emulsion 50 kg of the previously described preparation are emulsified in an oily phase such as 150 l of DRAGOXAT® (DRAGOCO) and 10.5 l of SPAN® 85 (ICI).

Depending on the size wanted for the spheres, the stirring is performed with a mechanical stirrer (size between 100 and 900 μm), or with an Ultra-turax® turning at 7,000 rpm (size ranging between 5 and 100 μm).

3. Crosslinking of the formed spheres

An oily phase containing 200 l of DRAGOXAT® and 18 kg of terephtalic acid dichloride is prepared under stirring. After complete dissolution of the acid dichloride, the oily phase is added under stirring to the emulsion described under (2).

The whole is left under stirring for 90 minutes, in order to induce a polymerization between, on the one hand, the activated diacid, and on the other hand, the alcohol functions of the polysaccharide. This reaction is helped in basic medium, and relatively long reaction times are necessary for the crosslinking to be sufficiently intense.

4. Presentation of the spheres

After reaction, the spheres are recovered by decanting or by centrifuging, depending on their size.

They are washed several times, and then placed in suspension in an organic or inorganic gel or solution.

They can be used as they are in foods, cosmetics or pharmaceutics.

EXAMPLE 2

Colored polysaccharide-based spheres

During step (2) of Example 1, 0.75 kg of pearly pigment (FLAMENCO) is added to the 50 kg of the polysaccharide-containing preparation.

All the other steps remain identical. It is also possible to encapsulate a lot of non-soluble pigments and the color of the spheres can be modified as anyone may wish.

EXAMPLE 3

Polysaccharide-based spheres containing an aqueous active ingredient

During step (1), 8.8 kg of carob flour are placed in suspension in 400 kg of deionized water.

During step (2), to 30 kg of the preparation described in (1) are added 20 kg of an aqueous solution containing the active ingredient. An aqueous extract of GINKGO BILOBA, or of ORCHID, or of any other plant is a suitable example.

After mixing the two compounds intimately, the preparation is emulsified, the spheres are crosslinked and then washed as described in Example 1.

EXAMPLE 4

Polysaccharide-based spheres containing a water-soluble powder or a reagent in non-soluble form As for Example 3, a preparation of carob flour is made, and then to 40 kg of said preparation are added 1 to 10 kg of an active ingredient in powdered form which is either water-soluble or not.

Suitable examples of active ingredients thus encapsulated are plant extracts (ALBAN, MULLER, WILLIAM RANSOM), animal or vegetable powdered active ingredients, micronized algae and plants, or any other dry extract.

After mixing intimately, the preparation is emulsified, the spheres are crosslinked and then washed as described in Example 1.

EXAMPLE 5

Polysaccharide-based spheres containing an oily or liposoluble active ingredient After preparation of the polysaccharide gel as described in Example 1, a first oil-in-water emulsion is prepared, whether or not in the presence of an emulsion-stabilizing agent (colloids, macromolecules, emulsifiers), where the oily phase is the phase containing the active ingredient, and where the aqueous phase is the polysaccharide-based gel.

Thus for example, to 30 kg of the polysaccharide-based preparation are added 1 to 20 kg of an oily phase such as palmitate of Vitamin A or acetate of vitamin E.

After strong stirring using any mechanical means capable of producing a very fine emulsion (turbine, Ultra-turax, ultrasounds), the intimate mixture is emulsified, the spheres are crosslinked and then washed as described in Example 1.

In all the preceding examples, the word spheres has been used but it also includes the capsules. Moreover, the obtained spheres or capsules can be used as they are in foods, cosmetics or pharmaceutical products. Within these preferred uses, an active ingredient is also encapsulated such as for example described in Examples 3 to 5.

Moreover, the examples have been given using as polysaccharide a carob flour containing no galactomannans. It is also possible to use as polysaccharides, carrageenans, glucomannans, natural gums, amylose or amylpectine or polysaccharides issued from fermentation. It is however preferred to use a galactomannan, in particular carob, as very good yields are then obtained with a simple process usable at an industrial level, notably at the food, cosmetic or pharmaceutical level.

It is also possible to use chemically modified polysaccharides containing primary alcohol functions spaced from the polymer chain in order to be more readily accessible particularly as regards a possible reaction with a crosslinking agent, for forming microspheres or microcapsules according to the present invention. It is thus possible to use hydroxyalkyl derivatives of polysaccharides, in particular $C_1$–$C_{30}$ hydroxyalkyl derivatives and notably $C_1$–$C_{30}$ hydroxyalkyl derivatives of cellulose. The following example constitutes an example of embodiment of this category.

EXAMPLE 6

Polysaccharide-based spheres obtained from chemically modified polysaccharides

The procedure is as described in Example 1, except that preparation step 1 uses a chemically modified polysaccharide available on the market, such as hydroxyethylcellulose of Natrosol 250® type sold by the company Aqualon, in lieu and place of a carob polysaccharide. The polysaccharide is prepared as follows:

12 kg of hydroxymethylcellulose available on the market under the commercial name Natrosol 250® from Aqualon are placed in suspension in 400 kg of cold deionized water, thereby giving a concentration of 3% by weight of chemically modified polysaccharide. The preparation is then heated to 40° C. for one hour under stirring in order to obtain a very homogeneous preparation. After cooling down to around room temperature, 20 kg of $NaHCO_3$ are added under strong stirring. After complete dissolution, the pH is stabilized to a value ranging between 8 and 8.4.

The rest of the preparation process is as in Example 1.

Accordingly, the invention covers all the means which constitute technical equivalents of the described means as well as the different combinations thereof.

We claim:

1. A microcapsule product, said product comprising a wall consisting essentially of a polysaccharide having primary alcohol functions crosslinked by interfacial crosslinking with a crosslinking agent.

2. The product of claim 1, wherein said polysaccharide has a molecular weight higher than 5000 Daltons.

3. The product of claim 1, wherein said polysaccharide has diosidic moieties and comprises from 1 to 4 primary alcohol functions per diosidic moiety.

4. The product of claim 1, wherein said polysaccharide is selected from the group consisting of a natural polysaccharide, a natural gum, amylose, amylopectine, a polysaccharide obtained by fermentation, a chemically modified polysaccharide comprising primary alcohol groups spaced from the polymer chain having improved reactivity with said crosslinking agent, and mixtures thereof.

5. The product of claim 4, wherein said chemically modified polysaccharide is a $C_1$–$C_{30}$ hydroxyalkyl polysaccharide.

6. The product of claim 1, wherein said product contains an active ingredient.

7. The product of claim 6, wherein said active ingredient is selected from the group consisting of a food active ingredient, a cosmetic active ingredient and a pharmaceutical active ingredient.

8. The product of claim 1, wherein said polysaccharide is selected from the group consisting of a galactomannan, a carrageenan, a glucomannan and mixtures thereof.

9. A method for preparing a microcapsule product, comprising the following steps:

dispersing or dissolving in an aqueous phase a polysaccharide having primary alcohol functions to obtain an aqueous phase containing said polysaccharide in dispersion or in dissolved state, placing said aqueous phase in contact with an organic phase non-miscible with water and containing a crosslinking agent having functions capable of reacting preferentially with the primary alcohol functions of the polysaccharide to produce an interfacial crosslinking of said primary alcohol functions of the polysaccharide during a period of time sufficient to obtain said product comprising a wall consisting essentially of a polysaccharide having primary alcohol functions crosslinked by interfacial crosslinking with said crosslinking agent, and separating said product from the reaction medium.

10. The method of claim 9, wherein said aqueous phase is an alkaline aqueous phase.

11. The method of claim 10, wherein said alkaline aqueous phase has a pH ranging between about 7.1 and about 10.

12. The method of claim 9, wherein said crosslinking agent is selected from the group consisting of an acid dichloryde and an acid dianhydride, thereby forming ester bonds in said product.

13. The method of claim 9, wherein said polysaccharide is present in the aqueous phase at a concentration ranging between 0.2% and 30% by weight of said aqueous phase.

14. The method of claim 9, wherein said polysaccharide is heated for a period of time sufficient to reach the total solution of the polysaccharide and thereafter the aqueous phase containing said solved polysaccharide is cooled down to room temperature.

15. The method of claim 9, wherein said organic phase comprises an organic liquid selected from the group consisting of a vegetable oil, a fatty acid ester, a mineral oil, a silicone and an apolar organic solvent.

16. The method of claim 9, wherein said organic phase is an oily phase containing an emulsifying agent and an emulsion is prepared.

17. The method of claim 9, comprising intimately mixing an active ingredient in the aqueous phase containing the polysaccharide.

18. The method of claim 17, wherein said active ingredient is a liposoluble active ingredient and an emulsion stabilizing agent is added to the organic phase.

19. The method of claim 18, wherein said emulsion stabilizing agent is selected from the group consisting of a colloid, a macromolecule, a natural emulsifier and a synthetic emulsifier.

20. The method of claim 9, wherein the proportion by weight of the crosslinking agent with respect to the weight of the polysaccharide containing aqueous solution ranges between about 20 and about 60%.

21. The method of claim 9, wherein said polysaccharide is selected from the group consisting of a natural polysaccharide, a natural gum, amylose, amylopectine, a polysaccharide obtained by fermentation, a chemically modified polysaccharide comprising primary alcohol groups spaced from the polymer chain more reactive with the crosslinking agent, and mixtures thereof.

22. The method of claim 21, wherein said natural polysaccharide is selected from the group consisting of a galactomannan, a carrageenan, and a glucomannan.

23. The method of claim 9, wherein said polysaccharide is a $C_1$–$C_{30}$ hydroxyalkyl polysaccharide.

24. A composition selected from the group consisting of a food composition, a cosmetic composition and a pharmaceutical composition, comprising a product selected from microcapsules and microspheres having a polysaccharide wall, wherein said polysaccharide comprises primary alcohol functions crosslinked by a crosslinking agent.

25. The composition of claim 24, wherein said product contains an active ingredient selected from the group consisting of a food active ingredient, a cosmetic active ingredient and a pharmaceutical active ingredient.

* * * * *